United States Patent [19]

Stanbro et al.

[11] Patent Number: 4,935,207
[45] Date of Patent: Jun. 19, 1990

[54] CAPACITIVE CHEMICAL SENSOR USING AN ION EXCHANGE SURFACE

[75] Inventors: William D. Stanbro, Columbia; Arnold L. Newman, Kensington, both of Md.

[73] Assignee: The Johns Hopkins University, Baltimore, Md.

[21] Appl. No.: 368,926

[22] Filed: Jun. 19, 1989

Related U.S. Application Data

[63] Continuation of Ser. No. 847,073, Apr. 1, 1986, abandoned.

[51] Int. Cl.[5] ............................................. G01N 27/22
[52] U.S. Cl. ..................................... 422/68.1; 422/69; 422/90; 422/98; 435/817; 436/806; 436/150
[58] Field of Search ....................... 422/68, 69, 90, 98; 436/150, 806; 338/34, 35; 324/60 R, 60 C, 61 R; 435/817

[56] References Cited

U.S. PATENT DOCUMENTS

| | | | |
|---|---|---|---|
| 4,343,688 | 8/1982 | Harwood | 204/430 |
| 4,386,336 | 5/1983 | Kinomoto | 338/35 |
| 4,520,341 | 5/1985 | Miyoshi | 338/35 |
| 4,562,725 | 1/1986 | Oka et al. | 204/430 |
| 4,571,543 | 2/1986 | Raymond et al. | 324/61 R |

FOREIGN PATENT DOCUMENTS

| | | | |
|---|---|---|---|
| 54-80191 | 6/1979 | Japan | 338/35 |
| 2137361 | 10/1984 | United Kingdom . | |

Primary Examiner—Michael S. Marcus
Attorney, Agent, or Firm—Robert E. Archibald; Howard W. Califano

[57] ABSTRACT

A capacitive chemical sensor is disclosed that uses an ion exchange layer to detect analyte ions in a liquid medium. An exchange mechanism occurs on the surface of the ion exchange layer, wherein a portion of the counter-ions are removed from the surface in favor of analyte ions. The resulting movement of counter-ions from the surface of the ion exchange layer alters the dielectric constant of the liquid medium along the surface of the ion exchange layer. This change in dielectric constant produces a change in capacitance of the capacitive chemical sensor.

26 Claims, 3 Drawing Sheets

● ≡ PRE-LOADED COUNTER-ION (22)

X ≡ ANALYTE (24)

● ≡ PRE-LOADED COUNTER-ION (22)
X ≡ ANALYTE (24)

CAPACITIVE CHEMICAL SENSOR USING AN ION EXCHANGE SURFACE

STATEMENT OF GOVERNMENTAL INTEREST

The Government has rights in this invention pursuant to Contract No. N00024-85-C-5301, awarded by the Department of the Navy.

This is a continuation of co-pending application Ser. No. 06/847,073 filed on Apr. 1, 1986 abandoned.

BACKGROUND OF THE INVENTION

1. Field of the Invention

The present invention relates to a capacitive chemical sensor that uses an ion exchange surface to detect analyte ions in a liquid medium.

2. Description of the Prior Art

Various capacitive sensors are taught in the art to detect humidity in the air or anesthetic gas in a gas mixture delivered to a patient during various medical procedures U.S. Pat. No. 3,350,941 issued to K. W. Misevicc et al. and U.S. Pat. Nos. 4,203,087 and 4,277,742 issued to Kovac et al, disclose capacitive humidity sensors. These humidity sensors use a moisture sensitive layer which absorbs water vapor. The dielectric property of the layer changes as it is penetrated by water vapors. As the moisture content of the air increases the capacitance of the humidity sensor increases.

U.S. Pat. No. 4,453,126 issued to G. A. Volgyesi and a published U.K. patent application GB No. 2 137 361 A, teach an apparatus for measuring anesthetic gas in a breathing mixture supplied to a patient. For both references, a planar capacitor is coated with a polymeric or lipid layer. The physical or chemical properties of the polymeric or lipid layer change with increasing concentration of the anesthetic gas, causing a change in the dielectric constant of the layer.

Similarly, U.S. Pat. No. 4,264,331 issued to Klein et al discloses an air pollutant and/or fire combustion sensing apparatus using a capacitive sensor. Physical absorption of the analyte gas into a coating changes the dielectric properties of the coating.

A related U.S. patent application filed by Arnold L. Newman on Nov. 19, 1985, entitled "Capacitive Chemical Sensor for Chemical Analysis and Measurement" (Ser No. 799,716) discloses a capacitive chemical sensor utilizing biochemical bonding systems; another related application filed by the present inventors and entitled "Capacitive Chemical Sensor for Detecting Certain Analytes, including Hydrocarbons in a Liquid Medium" discloses a capacitive chemical sensor relying on the affinity of an "active layer" for analyte molecules in solution.

SUMMARY OF THE INVENTION

The present invention is a new type of capacitive chemical sensor that utilizes an ion exchange layer. The ion exchange layer may have strong cation exchange sites, weak cation exchange sites, strong anion exchange sites or weak anion exchange sites. The surface of the ion exchange layer is exposed to a liquid medium containing a counter-ion. The counter-ion is usually a relatively large ion compared to a water molecule and has a dielectric constant significantly different from the water molecules. The counter-ions in solution are in equilibrium with the counter-ions that are attached to the ion exchange layer. However, when smaller analyte ions are introduced into the liquid medium, equilibrium is disturbed and a portion of the counter-ions are removed from the surface of the ion exchange layer. Exchange of the counter-ions from the surface of the ion exchange layer causes the influx of higher dielectric water molecules into the volume once occupied by the counter-ions. As a result, the dielectric properties of the liquid medium in the volume close to and above the ion exchange layer change, thus altering the measured capacitance of the sensor.

The invention uses an "open" or planar capacitor that comprises: a first and second conductor or electrode positioned on a substrate and dispose a distance from each other to form a channel; a first electrical insulating layer that covers the conductors; and, an ion exchange layer, which then coats the two insulated conductors and may fill a portion of the channel formed between the conductors. When an alternating voltage is applied across the conductors, an electric field is generated having lines of flux that cross the channel and bridge the volume between the conductors.

The present invention also teaches a differential sensor embodiment comprising the ion exchange capacitive sensor, as described above, with a reference capacitive sensor. The accuracy of the present invention is increased if differential sensing is employed. The reference capacitor compensates for changes in the dielectric constant of the liquid medium caused by changes in temperature, general ionic concentration and the physical and chemical state of the liquid medium.

A first novel feature is the use of an ion exchange layer to alter the dielectric properties in the liquid medium above the surface of the ion exchange layer.

A second novel feature is the utilization of an ion exchange mechanism, wherein a portion of the counter-ions attached to the surface of an ion exchange layer are removed in response to an increase in analyte concentration; wherein the volume once occupied by the counter-ions adjacent to the ion exchange surface is filled with higher dielectric fluid molecules.

A third novel feature is the use of a differential sensor having an ion exchange capacitive sensor and a reference capacitive sensor. The reference capacitive sensor compensates for changes in the dielectric constant of the liquid medium caused by changes in temperature, general ionic concentration or other physical or chemical states of the liquid medium.

DETAILED DESCRIPTION OF THE PREFERRED EMBODIMENT

Figure 1A:
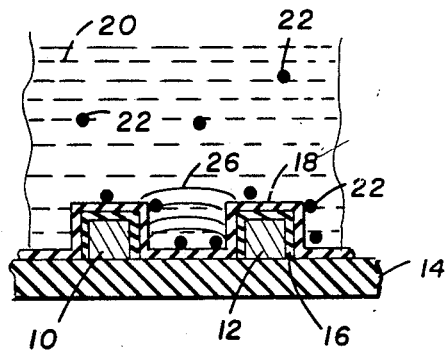
FIG. 1a illustrates the initial equilibrium condition; and, FIG. 1b illustrates displacement of the counter-ions from the surface of an ion exchange layer with the introduction of analyte into the liquid medium.
Figure 1B:
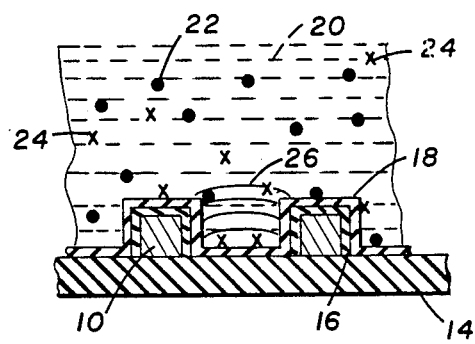
FIG. 1 is a schematic cross-sectional view of the invented capacitive chemical sensor using an ion exchange layer.

FIGS. 1a and 1b are schematic cross-sectional views showing the general configuration of the capacitive chemical sensor. A first conductor 10 and a second conductor 12 are positioned on the surface of an insulating material or substrate 14. A first layer containing an electrically insulated material 16 coats the two electrodes. An ion exchange layer 18 also coats the two electrodes and may partially fill the channel formed between the two electrodes. The ion exchange layer 18 is selected to have positive or negative sites and is exposed to a liquid medium 20 containing counter-ions 22 in solution. The counter-ions have an opposite sign from the positive or negative sites on the ion exchange layer. As will be described later in this specification, the liquid medium 20 may be an aqueous solution and the counter-ions 22 may include certain protein or fatty acid molecules. As shown in FIG. 1a, an equilibrium will be established between the counter-ions 22 attached to the surface of the ion exchange layer 18 and the counter-ions 22 remaining in the bulk solution. This equilibrium will reflect the ionic composition of the liquid medium.

FIG. 1b illustrates the ion exchange that occurs when an analyte 24 is added to the liquid medium. When an analyte 24 in sufficient concentration is introduced into the liquid medium, there will be competition with the counter-ions 22 for the functional charge sites on the surface of the ion exchange layer 18. A portion of the counter-ions 22 which had been attached to the ion exchange layer 18 will be released into the bulk solution and exchanged for analyte ions. The composition of ions bound to the surface of the ion exchange layer 18 thus changes. The resulting ion exchange modifies the dielectric constant of the liquid medium adjacent to the surface of the ion exchange layer 18.

When an alternating voltage is applied across the electrodes (10, 12), an electric field is generated having electrical lines of flux 26. The electric field will be larger within the channel and near the electrodes, and will decrease as one moves away from the electrodes. The capacitance of the sensor varies as the ion exchange mechanism changes the dielectric constant of the liquid medium in these higher field regions. The capacitance change can be measured using known electronic apparatus, such as a GenRad 1657 RLC Digibridge. Two possible mechanism account for the change in the dielectric constant within this electric field region. The first mechanism involves moving molecules of water into the region of high electric field intensity. The counter-ions 22 are generally larger than the water molecules (by an order of $10^2$ to $10^4$, or larger) and generally have a dielectric constant significantly smaller than water. When the counter-ions are attached to the surface of the ion exchanged layer 18, they displace water molecules from this region. The analyte ions 24 are generally significantly smaller than the counter-ions 22 and displace less water molecules. As discussed above, the ion exchange mechanism causes the movement of the larger counter-ions 22 from the surface of the ion exchange layer 18 back into bulk solution. This movement causes the higher dielectric water molecules to fill the volume previously occupied by counter-ions near the surface of the ion exchange layer 18. This movement of water molecules into the higher field region near the surface of the ion exchange layer 18 from the lower field regions in the bulk solution, increases the dielectric constant and increases the measured capacitance of the sensor. To maximize the change in capacitance for increasing analyte concentration, one would choose a counter-ion 22 with a large volume compared to the fluid molecules and with a dielectric constant significantly different from the fluid molecules.

The second mechanism, involves the replacement of a portion of the counter-ions 22, having a first dielectric constant, with analyte ions, having a second significantly different dielectric constant. As discussed previously, the ion exchange mechanism causes a portion of the counter-ions to be displaced from the surface of the ion exchange layer 18 and a portion of the analyte ions to attach to the surface of the ion exchange layer 18. For example, exchanging lower dielectric counter-ions 22 for higher dielectric analyte ions 24, will increase the measured capacitance.

Figure 2:
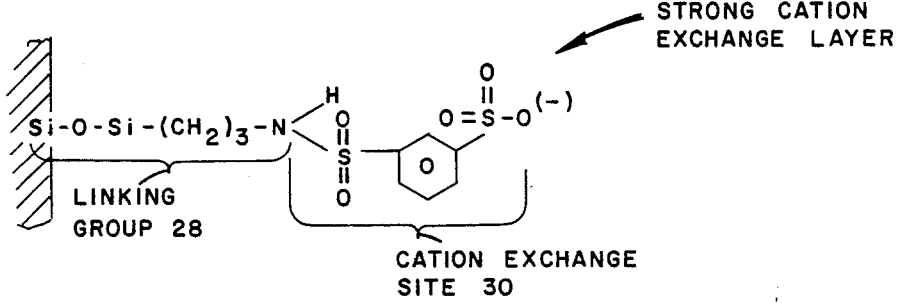
FIG. 2 is a chemical diagram of a strong cation exchange layer.
Figure 3:
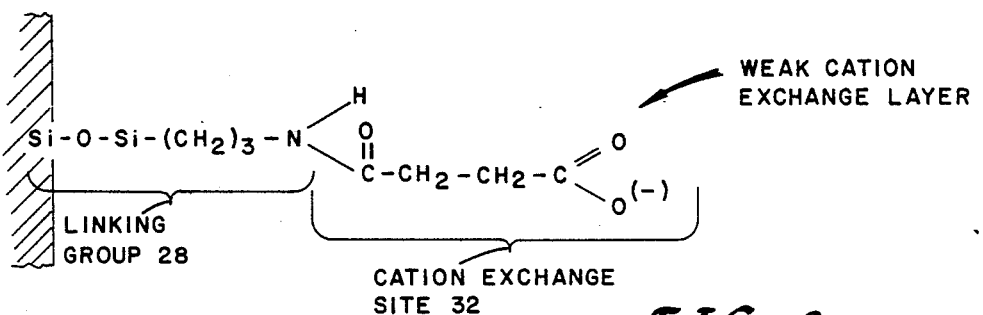
FIG. 3 is a chemical diagram of a weak cation exchange layer.
Figure 4:
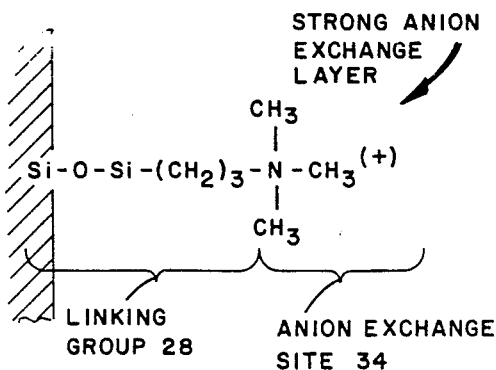
FIG. 4 is a chemical diagram of a strong anion exchange layer.
Figure 5:
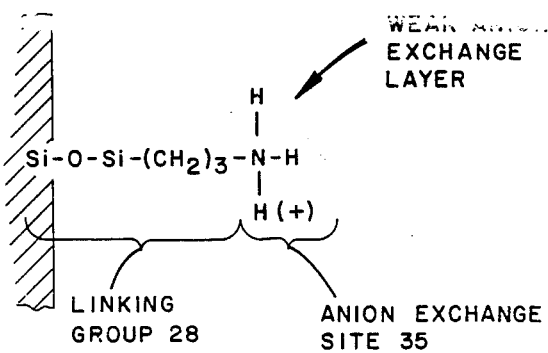
FIG. 5 is a chemical diagram of a weak anion exchange layer.

FIGS. 2 through 4 show four different types of ion exchange layers; (1) a strong acid cation exchange layer is shown in FIG. 2; (2) a weak acid cation exchange layer is shown in FIG. 3; (3) a strong anion exchange layer is shown in FIG. 4; and (4) a weak anion exchange layer is shown in FIG. 5. Production of all four layers starts with coating the surface electrodes (10, 12) with an electrically insulating layer, such as SiO, and then coating the insulating layer with a molecular linking chain. Applicants suggest the following procedure, although it is to be understood that this procedure is merely by way of example and that other linking groups could be used with a different derivatization procedure:

1. The conductors of the capacitive chemical sensor are coated with a 0.3 micron thick layer of SiO; and,
2. Propylamine groups are attached to the SiO surface layer, using the following steps:
   a. soak the substrate in 10% γ-aminopropyl-triethoxysilane $[(EtO)_3\text{-}S_i\text{-}(CH_2)_3\text{-}NH_2]$ and dry toluene overnight at room temperature.
   b. wash with dry toluene; and
   c. dry at 60° C. for 2 hours.

To produce the strong cation exchange layer shown in FIG. 2, the surface derivatized with the linking group 28 (such as the amino linking group outlined above) is reacted with benzene disulfonyl chloride to produce a sulfonamide linkage between the amine linking group and the benzene ring. The other, unreacted sulfonyl chloride group can then be hydrolyzed to sulfonic acid, which forms the cation exchange site 30. Applicants suggest, by way of example, the following procedure:

1. Cover the surface of the capacitive chemical sensor previously derivatized with an amine linking group, with a solution of 1 g of benzene disulfonyl chloride in 10 ml of pyridine.
2. Allow to sit for 30 minutes and then rinse thoroughly with distilled water.

The resulting strong acid cation exchange layer, shown in FIG. 2, comprises a linking group 28 and a cation exchange site 30. The cation exchange site 30 is negatively charged and will attract a positive counter ion 22 (see generally FIG. 1b). The strong cation exchange layer would be used to detect positive analyte ions in the liquid medium. It of course is to be understood, that other linking groups and other cation exchange groups can be used to form the cation exchange layer 18.

FIG. 3 illustrates a typical weak acid cation exchange layer comprising a linking group 28 and a cation exchange site 32. To produce this layer, the surface of the capacitive sensor is first derivatized with a linking group, such as the amino linking group described above. The derivatized surface is then reacted with excess succinyl chloride to form an amide linkage between the amino linking group 28 and the succinyl group. The unreacted acid chloride portion can then be hydrolyzed to a carboxylate group. At a sufficiently high pH the carboxylic acid is ionized forming the cation exchange site 32. Applicants suggest, by way of example, the following procedure:

1. Cover the surface of the capacitive chemical sensor previously derivatized with an amino linking group, with a solution of 1 g of succinyl chloride in 10 ml of pyridine.
2. Allow it to sit for 30 minutes and then rinse thoroughly with distilled water.

The cation exchange layer produced in this manner is considered "weak" because the acid only becomes partially ionized. This ion exchange layer has a cation exchange site 32 that is negatively charged and will attract a positive ion 22 (see generally FIG. 1b). The weak cation exchange layer, shown in FIG. 3, could be used to detect positive ions in the liquid medium. It of course is to be understood, that other linking groups and other cation exchange groups can be used to form the weak cation exchange layer.

FIG. 4 illustrates a typical anion exchange layer comprising a linking group 28 and an anion exchange site 34. To produce this layer, the surface of the capacitive sensor is first derivatized with a linking group, such as the amino linking group outlined above. The derivatized surface is then reacted with iodomethane until it is exhaustively methylated. This results in the formation of a tetramethyl quarternary ammonium salt that has a positive charge and therefore forms the ion exchange site 34. Applicants suggest, by way of example, the following procedure:

1. Cover the surface of the capacitive chemical sensor previously derivatized with an amino linking group, with iodomethane.
2. Heat gently for 10 minutes and then cool to room temperature and rinse twice with ethanol.

The ion exchange layer thus produced has an anion exchange site 34 that is positively charged and will attract a negative counter ion 22 (see, generally FIG. 1b). The anion exchange layer, shown in FIG. 4, would be used to detect negative ions in the liquid medium. It is of course to be understood, that other linking groups and other anion exchange groups can be used to form the anion exchange layer.

FIG. 5 illustrates a typical weak anion exchange layer comprising a linking group 28 and weak anion exchange site 35. To produce this layer, the surface of the capacitive sensor is first derivatized with the amino linking group, as described above. In a sufficiently low pH medium, the amino group becomes ionized. This forms the weak anion exchange sites 35.

The anion exchange layer produced in this manner is considered "weak" because the amino group only becomes partially ionized. This ion exchange layer has anion exchange sites 35 that are positively charged and will attract a negative ion 22 (see generally FIG. 1b). The weak anion exchange layer, shown in FIG. 5, could be used to detect negative ions in the liquid medium. It of course is to be understood, that other linking groups and other weak anion exchange groups can be used to form the weak anion exchange layer.

As best shown in FIG. 1A, the capacitive chemical sensor is preloaded with a liquid medium 20 containing counter-ions 22 in solution. Applicants have found that protein molecules or fatty acids provide excellent counter-ions. Protein molecules contain carboxylic acid groups and amino groups. With appropriate pH levels, the carboxylic acid groups will carry a negative charge and will be attracted to an anion exchange layer. Similarly, with appropriate pH levels, the amino groups will carry a positive charge, and will be attracted to a cation exchange layer. Fatty acids contain carboxylic acid groups, and with the correct pH, will carry a negative charge. These counter-ions were chosen because they are large compared to water molecules and have a dielectric constant lower than water. Typical protein molecules would be $10^2$ to $10^4$ or more, times larger than a water molecule; and, fatty acids would be $10^1$ to $10^2$ times larger than water molecules. However, it is to be understood that other counter-ions could be used and that the response of the sensor would be maximized when the counter-ions are considerably larger than water molecules and have a dielectric constant significantly different from water molecules. Similarly, a detection system could be made with counter-ions and analyte ions of the same size, if their dielectric constants are significantly different. In operation, a sensor preloaded with large protein molecules (which have both cation and anion groups on it) would respond with an increase in capacitance if a portion of the protein molecules were displaced by a small analyte ion such as a chloride ion.

Figure 6:
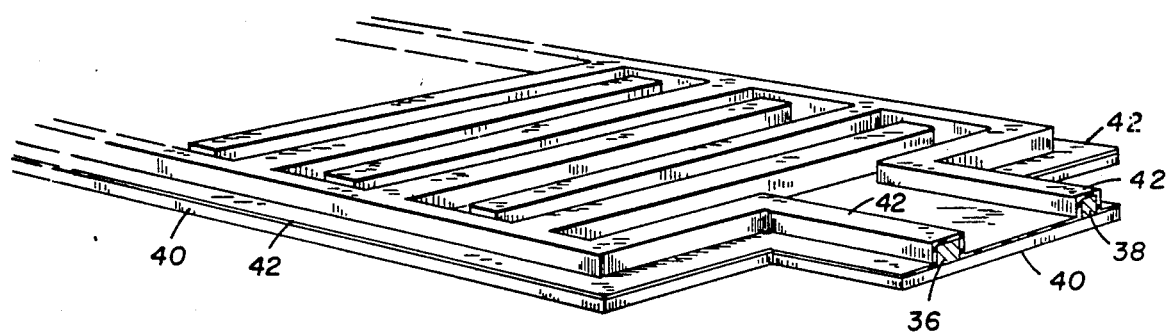
FIG. 6 is a perspective view of an "open" capacitor that uses a plurality of interdigitated fingers.

FIG. 6 is a perspective view of a planar capacitor having a plurality of interdigitated fingers. Metallic electrodes or conductors 36 and 38 are positioned on an insulating substrate 40. Each electrode has a plurality of fingers that are disposed in an interdigitated manner relative to the fingers of the other electrodes. The interdigitated fingers from both electrodes form a plurality of channels. Known photolithographic etching techniques are used to form the interdigitated fingers on a substrate. The substrate can be made from insulating material such as Corning 7059 glass or alumina wafers. The interdigitated fingers can be made of copper or gold. Applicants selected 2 mil wide fingers that are approximately 1 mil high and separated by 3 mil spaces, although other dimensions may be used. The interdigitated fingers are covered with an insulating layer 42. Applicants made the insulating layer 42 with a 114 2.5 micron coating of parylene polymer deposited using known deposition processes and a 0.3 micron coating of SiO deposited using vapor vacuum evaporation deposition; however, alternative electrical insulating material can be used. To complete the sensor, an ion exchange layer coats the insulating layer 42. (The ion exchange layer 18 is best shown in FIG. 1a). Liquid to be tested for a particular analyte ion is brought into contact with the planar capacitor as discussed earlier. It is to be understood that other geometries of the planar capacitor can provide the desired feature of the open capacitor. For example, the electrode elements of the capacitor can be interleaved on a substrate or, parallel electrode elements can be embedded in a molded insulator with the ion exchange layer coating the molded insulator. Further, the electrode elements 36 and 38 of the capacitor can be made from electrically conductive material or doped semiconductor materials, such as doped silicon.

It is also to be understood that, the invention will work with aqueous solutions that have different salt contents. Further, it is to be understood that the liquid medium may be nonaqueous liquids, as long as a significant dielectric change will occur with the displacement of those liquid molecules by the mechanisms taught herein.

Figure 7:
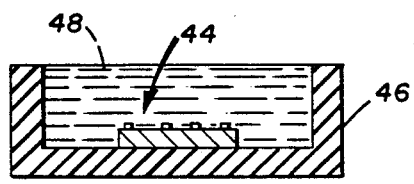
FIG. 7 is a schematic cross-sectional view of the ion exchange capacitive sensor positioned in a protective casing.

FIG. 7 is a schematic representation of the planar capacitor 44 (designed in accordance with the specification) and securely fixed in a casing 46. A molecular sieve membrane 48 allows solutions to enter the interior of the casing from the environment and to contact the sensor 44. The molecular sieve membrane 48 protects the sensor from abrasive particles in the environment and prevents the larger counter-ions from escaping from the casing, thereby allowing continuous or time trend measurements.

Figure 8:
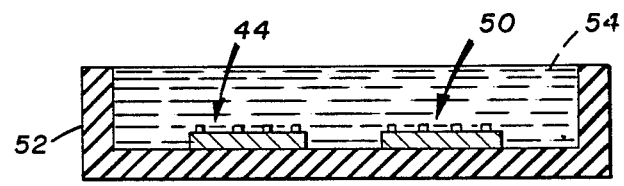
FIG. 8 is a schematic cross-section view of a differential capacitive sensor comprising an ion exchange capacitive sensor and a reference capacitive sensor.

FIG. 8 is a schematic representation of a differential sensor embodiment that includes both the ion sensor 44 and the reference capacitor 50. The accuracy of the present invention is increased if differential sensing is used. The reference capacitor 50 compensates for changes in the dielectric of the liquid medium caused by changes in temperature, ionic concentration, pH, composition and the physical and chemical state of the liquid medium. The reference capacitor 50 is identical in design to the ion exchange sensor capacitor, except the ion exchange layer is not used. Therefore, the reference capacitor comprises two electrodes positioned on a substrate coated with an insulating layer to form a capacitor. In the embodiment shown in FIG. 8, the ion exchange capacitive sensor 44 and the reference capacitor 50 are mounted within casing 52. A molecular sieve membrane 54 allows solutions to enter the interior of the casing from the environment and to contact both ion exchange capacitive sensor 44 and reference capacitor 50. The molecular sieve membrane 54 protects the sensor from abrasive particles in the environment and prevents the large counter-ions from escaping from the casing, thereby allowing continuous or time trend measurements.

Figure 9:
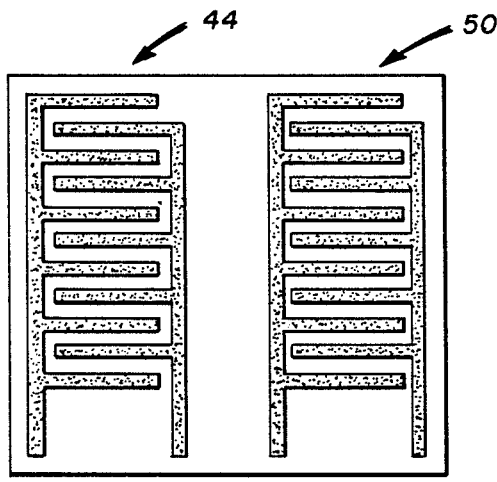
FIG. 9 is an embodiment of the differential capacitive sensor having the ion exchange capacitive sensor and the reference capacitive sensor located side by side.
Figure 10:
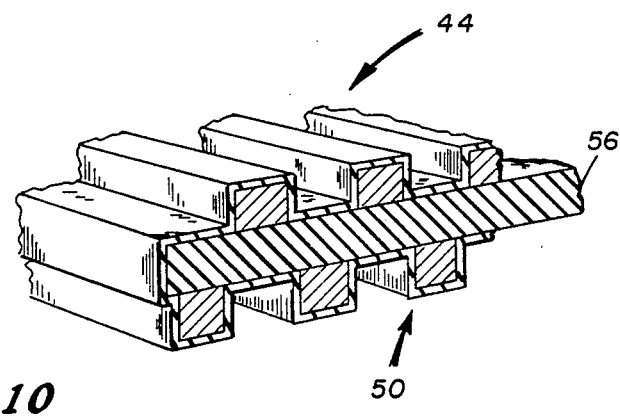
FIG. 10 is an embodiment of the differential capacitive sensor having the ion exchange capacitive sensor and the reference capacitor located back to back.

FIGS. 9 and 10 show various embodiments for a differential sensor that includes an ion exchange capacitive sensor 44 and a reference capacitor 50. FIG. 9 is a top view of the ion exchange capacitive sensor 44 and reference capacitor 50 located side by side on the same substrate. FIG. 10 is a cross-sectional view of the ion exchange capacitive sensor 44 and reference capacitor 50 located back to back. A shield 56 located between the capacitors can be used to isolate the electric field generated by each capacitor. With both the side by side and back to back embodiments, the fluid medium under test is adapted to contact the surface of both the ion exchange sensor capacitor 44 and reference capacitor 50. For simplicity of illustration, the ion exchange capacitive sensor shown in FIGS. 9 and 10 do not show the ion exchange layer that covers the insulating layer.

Figure 11:
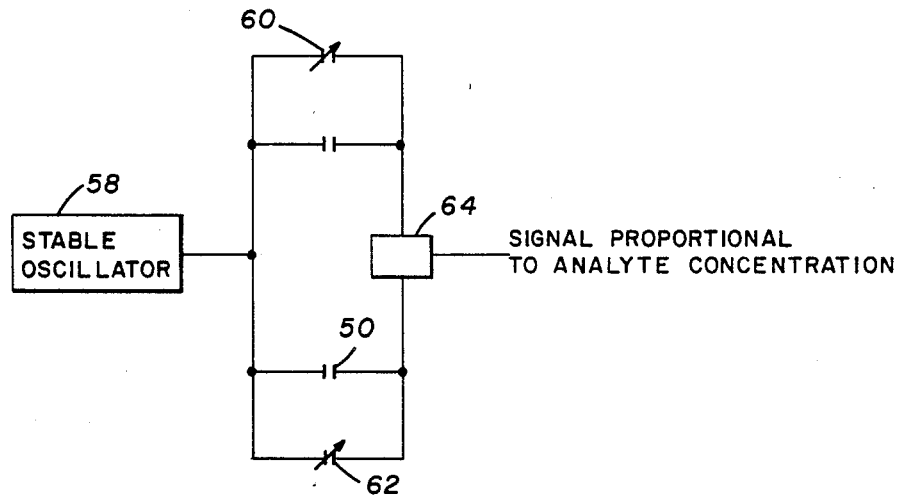
FIG. 11 is a schematic diagram of a circuit to detect the phase difference between the ion exchange capacitive sensor and the reference capacitor.
Figure 12:
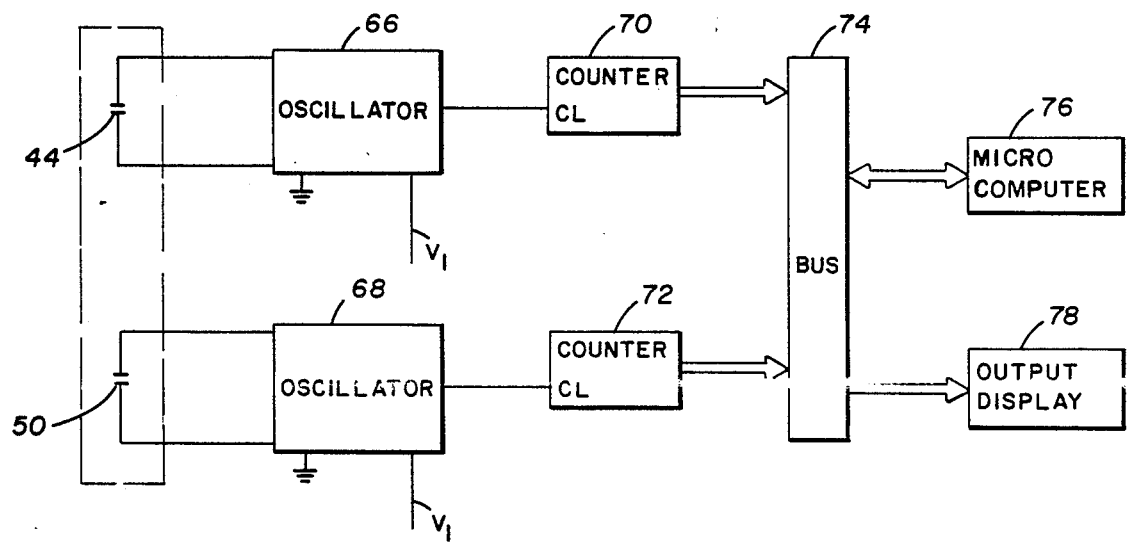
FIG. 12 is a schematic diagram of a microprocessor system for use with a differential capacitive sensor that has an ion exchange capacitive sensor and a reference capacitive sensor.

FIGS. 11 and 12 are schematic diagrams which illustrate two possible circuits to be used with a differential sensor as taught by the present invention. FIG. 11 is a schematic diagram of the circuit to detect the phase difference between the ion exchange capacitive sensor 44 and the reference capacitor 50. The stable oscillator 58 supplies an alternating signal to the ion exchange capacitor 44 and the reference capacitor 50. These capacitors are placed in parallel with trim capacitors 60 and 62. Phase detector 64 detects the phase angle shift between the ion exchange capacitive sensor 44 and the reference capacitor 53. The phase shift is functionally related to the analyte ion concentration in the fluid medium.

FIG. 12 is a schematic diagram of a microprocessor system for use with a differential sensor. The system contains an ion exchange capacitive sensor 44 and reference capacitor 50. The ion exchange capacitive sensor 44 and reference capacitor 50 are brought into contact with the liquid medium under test. Each capacitor is connected to an oscillator (66, 68) and a change in the capacitance will alter the frequency of oscillation of its associated oscillator. The output frequency of each oscillator (66, 68) is fed to an associated counter (70, 72), which sends the frequency count in digital form via bus 74 to microprocessor 76. A look-up table is stored in the microcomputer and a determination of the concentration of the analyte in the fluid medium is made. This value is displayed on output display 78. It is to be understood that other circuits can also be envisioned once one understands the differential change in capacitance between the ion exchange capacitor and the reference capacitor as taught the present invention. The ion exchange capacitive sensor may be integrated with the reference capacitor and signal processing electronics to form either a monolithic integrated chip or a hybrid circuit. For example, the ion exchange capacitive sensor could be integrated in the gate circuit of a field effect transistor (FET) to yield a "floating gate" FET configuration.

Obviously many modifications and variations of the present invention are possible in light of the above teachings. It is therefore to be understood that within the scope of the appended claims, the invention may be practiced otherwise than is specifically described.

What is claimed is:

1. A device for sensing analyte ions in a liquid, said device comprising:
 a capacitor having at least one pair of spaced apart electrode elements, said electrode elements adapted to create an electric field therebetween;
 an electrically insulating layer coating said electrode elements;
 a first layer of ion exchange molecules coating said electrically insulating layer;
 a second layer of counter-ion molecules attached to molecules of said first layer said second layer adapted to be covered by a test liquid containing analyte ions of interest so that counter-ion molecules are displaced from said first layer by said analyte ions in said test liquid until a dynamic equilibrium is obtained, said counter-ion molecules sized to be larger than analyte ions and to have a different dielectric constant than said test liquid; and, a means, associated with said capacitor, responsive to the average dielectric properties in a volume adjacent to said insulating layer, wherein displacement of said counter-ion molecules from attachment to said first layer alters said average dielectric properties.

2. The device of claim 1, wherein each of said ion exchange molecules includes a cation exchange site and wherein each of said counter ion molecules carries a positively charged site.

3. The device of claim 1, wherein each of said ion exchange molecules includes an ion exchange site and wherein each of said counter-ion molecules a negatively charged site.

4. The device of claim 1, wherein each of said electrode elements comprises a plurality of spaced apart finger electrodes.

5. The device of claim 1, wherein said counter-ion molecules are selected from the group consisting of protein molecules and fatty acids.

6. The device of claim 1, wherein said counter-ion molecules are large compared to water molecules and have a lower dielectric constant than water molecules.

7. The device of claim 1, wherein said electrode elements are made from doped semiconductor material.

8. The device of claim 1, wherein said electrical elements are made from electrically conductive material.

9. The device of claim 1, further comprising an electronic means, operably coupled to second capacitor, for measuring and displaying a change in capacitance.

10. The device of claim 1, wherein said capacitor is positioned in a chamber, said chamber adapted to be at least partially filled with said test liquid.

11. The device of claim 10, wherein said chamber includes an opening exposed to said test liquid containing analyte ions.

12. The device of claim 11, wherein a membrane covers said opening, said membrane having pores sized to prevent escape of counter-ion molecules from said chamber.

13. A differential sensor for sensing analyte ions in a liquid, comprising:
  a first capacitor having at least one pair of spaced apart electrode elements said first capacitor comprising,
  a. an electrically insulating layer covering said electrode elements,
  b. a first layer of ion exchange molecules coating said electrically insulting layer,
  c. a second layer of counter-ion molecules attached to molecules of said first layer, said second layer adapted to be covered by a test liquid containing analyte ions of interest so that counter-ion molecules are displaced from said first layer by said analyte ions in said test liquid until a dynamic equilibrium is obtained;
  a second capacitor having at least one pair of spaced apart electrode elements and a layer of electrically insulating material coating said spaced apart electrode elements of said second capacitor and adapted to be exposed to said test liquid; and,
  an electronic means, operably coupled to said first and second capacitor for calculating the analyte concentration of the test liquid wherein analyte ions in the test liquid will displace a portion of said counter-ions from the surface of said ion exchange layer thereby changing the capacitance of said first capacitor.

14. The device of claim 13, wherein said counter-ion molecules are selected from the group consisting of protein molecules and fatty acids.

15. The device of claim 13, wherein in said counter-ion molecules are large compared to water molecules and have a lower dielectric constant than water molecules.

16. The device of claim 13, wherein said counter-ion molecules are larger than the analyte ion.

17. The device of claim 13, wherein said electrode elements for said first and second capacitor are made from doped semiconductor material.

18. The device of claim 13, wherein said electrode elements for said first and second capacitor are made from electrically conducted material.

19. The device of claim 13, wherein each of said ion exchange molecules have a cation exchange side and wherein each of said counter-ion molecules carries a positively charged site.

20. The device of claim 13, wherein each of said ion exchange molecules have an ion exchange site and wherein each of said counter-ion molecules carries a negatively charged site.

21. The device of claim 13, wherein said first and second capacitors are positioned in a chamber.

22. The device of claim 21, wherein said chamber includes an opening exposed to said test liquid containing analyte ions.

23. The device of claim 22, wherein a membrane covers said opening, said membrane having pores sized to prevent counter ion molecules from escaping from said chamber.

24. A device for sensing analyte ions, said device comprising:
  a first capacitor having at least one pair of spaced apart electrode elements, said electrode elements adapted to create an electric field therebetween;
  an electrically insulating layer coating said electrode elements;
  a first layer of ion exchange molecules coating said electrically insulating layer;
  a counter-ion supplying liquid;
  a chamber means, surrounding said capacitor, for maintaining said counter-ion supplying liquid in contact with said first layer;
  a second layer formed from said counter-ions attached in dynamic equilibrium to molecules of said first layer and displaceable therefrom upon contact with analyte ions of interest, said counter-ion molecules sized to be larger than analyte ions and to have a different dielectric constant than said counter-ion supplying liquid; and,
  a first electric means, associated with said first capacitor, responsive to the average dielectric properties in a volume adjacent to said insulating layer, wherein displacement of said counter-ion molecules from attachment to said first layer alters said average dielectric properties.

25. The device of claim 24, wherein said chamber means includes a means for introducing a liquid contain analyte into said chamber means.

26. The device of claim 25, further comprising:
  a second capacitor having at least one pair of spaced apart electrode elements and a layer of electrically insulating material coating said spaced apart electrode elements of said second capacitor and adapted to be exposed to said liquid containing analyte; and, a second means, associated with said second capacitor, responsive to the average dielectric properties in a volume adjacent to said insulating layer.

* * * * *